United States Patent
Belzer et al.

(10) Patent No.: US 6,770,762 B2
(45) Date of Patent: Aug. 3, 2004

(54) PROCESS FOR PREPARING AND PURIFYING 1,7'-DIMETHYL-2'-PROPYL-2,5'-BI-1H-BENZIMIDAZOLE

(75) Inventors: Werner Belzer, St. Goar (DE); Rolf Dach, Gau-Algesheim (DE); Volker Fachinger, Nussbaum (DE); Markus Heitzmann, Ingelheim (DE); Hartmut Schmidt, Bockenau (DE)

(73) Assignee: Boehringer Ingelheim Pharma GmbH & Co. KG, Ingelheim (DE)

( * ) Notice: Subject to any disclaimer, the term of this patent is extended or adjusted under 35 U.S.C. 154(b) by 0 days.

(21) Appl. No.: 10/345,773

(22) Filed: Jan. 16, 2003

(65) Prior Publication Data

US 2003/0139608 A1 Jul. 24, 2003

Related U.S. Application Data

(60) Provisional application No. 60/386,123, filed on Jun. 5, 2002.

(30) Foreign Application Priority Data

Jan. 18, 2002 (DE) .......................... 102 01 725

(51) Int. Cl.$^7$ .............................................. C07D 403/04
(52) U.S. Cl. ...................................................... 548/305.4
(58) Field of Search ...................................... 548/305.4

(56) References Cited

U.S. PATENT DOCUMENTS 3,150,136 A 9/1964 Wolfrum et al.

OTHER PUBLICATIONS

Ries, U. J. et al: "6–Substituted Benzimidazoles as New Nonpeptide Angiotensin II Receptor Antagonists: Synthesis, Biological Activity, and Structure–Activity Relationships"; J. Med. Chem. 1993, vol. 36, pp. 4040–4051.

*Primary Examiner*—Laura L. Stockton
(74) *Attorney, Agent, or Firm*—Robert P. Raymond; Michael Morris; Philip I. Datlow

(57) ABSTRACT

Disclosed is a process which can be used on an industrial scale for preparing and purifying 1,7'-dimethyl-2'-propyl-2,5'-bi-1H-benzimidazole in which the crude product is subjected to charcoal treatment.

11 Claims, No Drawings

PROCESS FOR PREPARING AND PURIFYING 1,7'-DIMETHYL-2'-PROPYL-2,5'-BI-1H-BENZIMIDAZOLE

RELATED APPLICATIONS

Benefit of U.S. Provisional Application Serial No. 60/386,123, filed on Jun. 5, 2002 is hereby claimed and said application is herein incorporated by reference in its entirety.

FIELD OF THE INVENTION

The invention relates to a process for preparing and purifying 1,7'-dimethyl-2'-propyl-2,5'-bi-1H-benzimidazole which can be used on an industrial scale.

BACKGROUND OF THE INVENTION

The preparation of 1,7'-dimethyl-2'-propyl-2,5'-bi-1H-benzimidazole by reacting 2-propyl-4-methyl-1H-benzimidazole-6-carboxylic acid with N-methyl-o-phenylene-diamine dihydrochloride is known from J. Med. Chem. (1993), 36(25), 4040-51 and International Patent Application WO 0063158.

1,7'-dimethyl-2'-propyl-2,5'-bi-1H-benzimidazole is of major importance as an intermediate product in the industrial synthesis of pharmaceutically active substances, particularly the pharmaceutically active substance telmisartan (Drugs of the future 1997, 22(10), 1112–1116). This gives rise to the need for a high level of purity. The purification process using ethyl acetate and diethyl ether known from the abovementioned literature is unsuitable as a large-scale process as diethyl ether, for example, presents a safety problem and requires careful handling on account of its toxicity, its tendency to form peroxides and the risk of explosion of its vapours, e.g. by electrostatic discharge.

The aim of the present invention is therefore to provide a process which can be used on an industrial scale for purifying the 1,7'-dimethyl-2'-propyl-2,5'-bi-1H-benzimidazole prepared by the abovementioned methods of synthesis and the variants thereof described in this specification.

DETAILED DESCRIPTION OF THE INVENTION

Surprisingly it has been found that 1,7'-dimethyl-2'-propyl-2,5'-bi-1H-benzimidazole may be obtained in a highly pure form by a process suitable for use on an industrial scale if the essential purification steps are carried out using charcoal.

The invention therefore relates to a process which can be used on an industrial scale for purifying 1,7'-dimethyl-2'-propyl-2,5'-bi-1H-benzimidazole which has been prepared by reacting 2-propyl-4-methyl-1H-benzimidazole-6-carboxylic acid or the salts thereof with N-methyl-o-phenylene-diamine or the salts thereof, in which the crude product is treated with charcoal.

In a preferred process according to the invention 2-propyl-4-methyl-1H-benzimidazole-6-carboxylic acid is reacted with N-methyl-o-phenylene-diamine or the salts thereof, preferably in the form of a salt, preferably in the form of the phosphate, chloride or bromide salt, more preferably in the form of the phosphate or chloride salt, most preferably in the form of the phosphate salt, in the presence of methanesulphonic acid and phosphorus pentoxide.

Also preferred is a process wherein the reaction is carried out at a temperature of 125 to 145° C.

In a particularly preferred process, the charcoal treatment purification step is carried out after the end of the reaction, hydrolysis and pH adjustment, by adding the reaction mixture to the charcoal.

Also particularly preferred is a process wherein the charcoal treatment purification step is carried out at a temperature of 70 to 80° C.

Of particular importance is a process wherein the charcoal treatment purification step takes place at a pH of 0.7 to 1.2.

Also of particular importance is a process wherein the amount of charcoal used in a purification step is from 5 to 20 percent by weight of the 2-propyl-4-methyl-1H-benzimidazole-6-carboxylic acid used.

In a particularly preferred process, the purification step is repeated one to three times after the filtration or centrifugation of the reaction mixture.

In another particularly preferred process, after the purification by treatment with charcoal, the following steps take place in succession:

a) an organic solvent is added,
b) a base is added to obtain a pH of 5 to 6,
c) the aqueous phase is separated off,
d) the 1,7'-dimethyl-2'-propyl-2,5'-bi-1H-benzimidazole is separated from the organic phase by crystallization and subsequent filtration or centrifugation.

In another preferred process, isopropanol is used as the organic solvent in step a).

Also particularly preferred is a process wherein, in step b), the base is added at a temperature of 70 to 80° C.

Also particularly preferred is a process wherein, in step d), the crystallization is carried out by the addition of water.

1,7'-dimethyl-2'-propyl-2,5'-bi-1H-benzimidazole is used in particular for preparing telmisartan. Telmisartan may be prepared using the method described in Drugs of the future 1997, 22(10), 1112–1116 according to the following synthesis diagram I:

Diagram I:

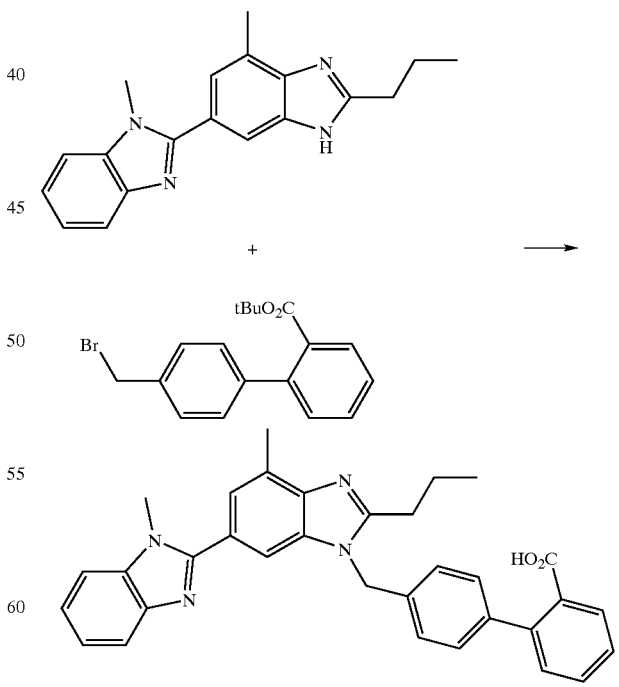

The following variants A, B, C, D and E are particularly preferred embodiments of the process according to the invention.

Variant A:

2-propyl-4-methyl-1H-benzimidazole-6-carboxylic acid (PMBC) and N-methyl-o-phenylenediamine (NMPD) or the salts thereof are added successively to a solution of an organic acid, preferably methanesulphonic acid, phosphorus pentoxide, thionyl chloride, sulphonyl chloride, acetic anhydride or polyphosphoric acid, preferably methanesulphonic acid, phosphorus pentoxide or thionyl chloride and/or mixtures or dilutions thereof with inert organic solvents, preferably N-methylpyrrolidinone, o-, m- or p-xylene, most preferably N-methylpyrrolidinone, with stirring at a temperature of 100 to 160° C., preferably at 115 to 150° C., particularly at 125 to 145° C., most preferably at about 135° C. PMBC and NMPD are used in a molar ratio of 1.0:0.5 to 1.0:2.0, preferably 1.0:0.7 to 1.0:1.5, more preferably 1.0:1.0.

The amount of organic acid and organic solvent is determined according to the amount of PMBC used. Up to 10 mol, preferably 2 to 8 mol, most preferably about 7 mol of organic acid and up to 2 mol, preferably 0.5 to 1.5 mol, most preferably about 1 mol of phosphorus pentoxide are used per mol of PMBC.

After the addition has ended the mixture is stirred for up to 10 hours, preferably 1 to 4 hours, most preferably 3 hours at a temperature of 100 to 160° C., preferably 125 to 145° C., preferably 135° C. Then, in order to hydrolyse the excess acid component (anhydride, acid chloride), water is added to the organic acid used, for example phosphorus pentoxide, at a temperature of not more than 100° C., preferably not more than 90° C., in a ratio of 1.0:2.0 to 1.0:0.1, preferably 1.0:1.4 to 1.0:0.2.

After hydrolysis is complete, the pH is adjusted to 0.2 to 1.8, preferably 0.5 to 1.5, most preferably 0.7 to 1.2, more preferably 0.9 by the addition of a base, preferably sodium hydroxide, sodium carbonate or an amine, most preferably sodium hydroxide, sodium carbonate, ammonia, pyridine or triethylamine, most preferably sodium hydroxide solution or ammonia, more preferably sodium hydroxide. The temperature of the reaction mixture should not exceed 100° C. during this addition and is preferably below 90° C., most preferably from 70–80° C.

While the temperature range remains constant, charcoal, preferably activated charcoal, preferably "dry activated charcoal", "moist activated charcoal" or "granulated activated charcoal", more preferably "dry activated charcoal" of the SX 2, SX Ultra or L2S grade is added to the reaction mixture to purify it. The activated charcoal preferably used in the process according to the invention may be obtained for example from the companies Norit, Atofina or Begerow. The amount of charcoal used in each purification step should be from 5 to 20 percent by weight, preferably from 6 to 15 percent by weight, most preferably from 8 to 12 percent by weight, more preferably about 10 percent by weight of the amount of PMBC used. The reaction mixture combined with charcoal is stirred for at least 5 min, preferably 5 to 60 minutes, preferably 8 to 50 minutes, most preferably 10 to 30 minutes at a temperature of max. 90° C., preferably at 50 to 80° C., most preferably at 70 to 75° C. and then filtered or centrifuged, preferably filtered. The purification step may be repeated one to ten times, preferably one to five times, most preferably one to three times, preferably twice, with the reaction mixture which has been filtered or centrifuged in each case.

Then an organic solvent, preferably n-butanol, tert.-butanol, 2-methyl-propanol, n-propanol, isopropanol, ethyl acetate, dichloromethane, tetrahydrofuran or toluene, preferably n-butanol or isopropanol, most preferably isopropanol, is added to the reaction mixture with stirring. The amount of solvent is determined by the amount of PMBC previously used in the process and should be from 1:1 to 20:1, preferably from 1:1 to 10:1, most preferably from 1:1 to 5:1, preferably 3:1.

After the addition of the solvent has ended, a base, preferably sodium hydroxide, sodium carbonate or an amine, such as e.g. ammonia, pyridine or triethylamine, most preferably sodium hydroxide or ammonia, more preferably sodium hydroxide, is added at a temperature of not more than 100° C., preferably at 50 to 90° C., most preferably at 70 to 80° C., more preferably at about 75° C., to obtain a pH of 4 to 8, preferably 5 to 7, more preferably about 5 to 6. The mixture is stirred for at least 5 minutes, preferably 10 to 30 minutes, while the temperature is kept constant. After the phase separation has ended the aqueous phase is separated off and discarded.

To crystallise the product, acetone, ethyl acetate or water, preferably acetone or water, most preferably water, is added to the organic phase at ambient temperature or elevated temperature, preferably by refluxing. The amount of water used corresponds to 50 to 200 percent by volume, preferably 70 to 150 percent by volume, preferably percent by volume, most preferably 80 to 130 percent by volume, more preferably 120 percent by volume of the organic solvent used.

After the water has been added the mixture is cooled to a temperature of not more than 40, preferably 5 to 30° C., most preferably 10 to 20° C., more preferably 15° C.

To isolate the product the mixture may be filtered or centrifuged. The product thus obtained may be treated with a washing solution containing water and one or more organic solvents selected from among acetone, n-butanol, tert.-butanol, cyclohexane, dichloromethane, ethyl acetate, isopropanol, methanol, 2-methyl-propanol, n-propanol, tetrahydrofuran, toluene or xylene, preferably acetone, isopropanol or ethyl acetate, most preferably isopropanol. As a rule the washing solution contains a ratio by volume of organic solvent/water of 1:0 to 1:10, preferably from 1:1 to 1:8, most preferably from 1:1.5 to 1:6, more preferably 1:2. Then the product is washed with water and dried, preferably in vacuo, at not more than 110° C., preferably not more than 100° C., most preferably at 75 to 90° C.

Variant B:

As a modification of Variant A the strongly acidic reaction solution can be filtered through charcoal-filled containers or cartridges at a pH of about 0.2 to 1.8, preferably 0.5 to 1.5, most preferably 0.7 to 1.2, more preferably 0.9, instead of adding charcoal to the reaction solution or adding the reaction solution to the charcoal. The purification of the filtrate by extraction with an organic solvent and the additional working up may be carried out as described in Variant A.

Variant C:

As a modification of Variant A, instead of treating the acidic to strongly acidic reaction solution with charcoal, it is possible to treat the organic product solution with charcoal, for example to add charcoal, to add it to charcoal or filter it through charcoal, and the additional working up may be carried out as described in Variant A.

Variant D:

As a modification of Variant A, B or C the extraction may be carried out with a larger amount of the organic solvent, also at lower temperature, and this may be reduced again before the precipitation.

Variant E:

Another possible way of obtaining 1,7'-dimethyl-2'-propyl-bis-1H-benzimidazole as a pure product comprises directly precipitating the reaction product once the reaction has ended and hydrolysing it by the addition of a sufficient quantity of a base, preferably sodium hydroxide, sodium carbonate or an amine, such as e.g. ammonia, pyridine or triethylamine, most preferably sodium hydroxide or ammonia, more preferably sodium hydroxide or ammonia or adding the reaction solution to a solution of the base. After subsequent filtration the crude product, which may be dried, is dissolved in an organic acid or an organic solvent or a mixture of solvents selected from among methanesulphonic acid, isopropanol, n-butanol, ethyl acetate, methanol or toluene, preferably methanesulphonic acid or isopropanol, and the charcoal purification steps with subsequent further working up are carried out as described in Variant A. If methanesulphonic acid is used the precipitation may also be carried out by the addition of an alcoholic, e.g. methanolic, sodium hydroxide solution or by piping the product solution into an alcoholic, for example methanolic, sodium hydroxide solution. In this variant ascorbic acid or BHT (2,6-di-tert-butyl-4-methoxyphenol) may be added, preferably ascorbic acid.

The following Examples serve to illustrate the preparation and purification of 1,7'-dimethyl-2'-propyl-2,5'-bi-1H-benzimidazole. They represent only possible methods, without restricting the broad scope of the present invention to their contents.

EXAMPLE 1 (Variant A)
Preparation and Purification of 1,7'-dimethyl-2'-propyl-2,5'-bi-1H-benzimidazole 70 kg of phosphorus pentoxide are dissolved (at 115–145° C.) in 300 kg of methanesulphonic acid. At 125–145° C., 100 kg of 2-propyl-4-methyl-1H-benzimidazole-6-carboxylic acid (PMBC) and 90 kg of N-methyl-o-phenylene-diamine (NMPD) are added to this solution. The reaction mixture is stirred for up to 4 hours at this temperature and then cooled to about 80° C. The mixture is quenched with about 350 l of water. The pH is adjusted to about 1 by the addition of about 180 kg of 50% sodium hydroxide solution. The strongly acidic reaction solution is combined with about 10 kg of activated charcoal and stirred for at least 5 minutes at 70–80° C. Then the charcoal is filtered off and washed with water. The charcoal treatment of the solution is repeated up to 3 times. About 400 l of isopropanol are added to the filtrate with stirring and the pH is adjusted to about 5 to 6 by the addition of about 190 kg of 50% sodium hydroxide solution. During the subsequent phase separation the lower aqueous phase is separated off and discarded. To precipitate the product about 420 l of water are added to the organic phase at reflux temperature. The mixture is cooled to about 20° C. The precipitated product is centrifuged off and washed with about 280 l of a 2:1 mixture of water and isopropanol and finally with about 70 l of water. The isolated product is dried for at least 5 hours at not more than 90° C. in vacuo. It has an HPLC purity of at least 99.5 percent by area. The yield is about 85% based on the PMBC used.

EXAMPLE 2 (Variant E)
Preparation and Purification of 1,7'-dimethyl-2'-propyl-2,5'-bi-1H-benzimidazole 70 kg of phosphorus pentoxide are dissolved at 115–145° C. in 300 kg of methanesulphonic acid. At 125–145° C., 100 kg of 2-propyl-4-methyl-1H-benzimidazole-6-carboxylic acid (PMBC) and 90 kg of N-methyl-o-phenylene-diamine (NMPD) are added to this solution. The reaction mixture is stirred for up to 4 hours at this temperature and then cooled to about 80° C. The mixture is quenched with about 540 l of water. To precipitate the product the pH is adjusted to 5 to 6 at 50–60° C. with about 370 kg of 50% sodium hydroxide solution. The product precipitated is centrifuged and washed with 780–1040 l of water and dried at not more than 90° C. in vacuo. The yield is 80–100% based on the PMBC used.

150 kg of 1,7'-dimethyl-2'-propyl-2,5'-bi-1H-benzimidazole and 3 kg of ascorbic acid (optional) are suspended in 285 l of water and combined with 94 kg of methanesulphonic acid. About 10 kg of activated charcoal are added to the strongly acidic solution and the suspension is stirred for at least 5 min. at 50 to 60° C. Then the charcoal is filtered off and washed with water. The charcoal treatment of the solution is repeated up to 6 times. In order to precipitate the product the filtrate is added to a solution of about 88 kg of 45% sodium hydroxide solution and 150 l of methanol at 60–80° C., with stirring. Alternatively, the methanolic sodium hydroxide solution may also be added to the filtrate. Then it is cooled to 10–25° C. and the pH is adjusted to about 9 to 12 with sodium hydroxide solution. Then the product is centrifuged and washed with about 700 l of water. The isolated product is dried at not more than 90° C. in vacuo. It has an HPLC purity of about 99.0 percent by area. The yield is about 85% based on the 1,7'-dimethyl-2'-propyl-2,5'-bi-1H-benzimidazole used.

EXAMPLE 3 (Variant C)
Purification of 1,7'-dimethyl-2'-propyl-2,5'-bi-1H-benzimidazole 150 kg of 1,7'-dimethyl-2'-propyl-2,5'-bi-1H-benzimidazole are dissolved at 70–80° C. in 750 l of isopropanol and combined with 7 kg of charcoal. After a minimum of 5 minutes' stirring the charcoal is separated off and washed with about 70 l of isopropanol and about 145 l of water. The charcoal treatment is repeated up to 3 times. To precipitate the product, about 420 l of water are added to the organic phase at reflux temperature. The mixture is cooled to about 20° C. The precipitated product is centrifuged off and washed with about 400 l of a 2:1 mixture of water and isopropanol and lastly with about 70 l of water. The isolated product is dried for at least 5 hours at not more than 90° C. in vacuo. It has an HPLC purity of at least 99.5 percent by area. The yield is 85–95% based on the 1,7'-dimethyl-2'-propyl-2,5'-bi-1H-benzimidazole used.

What is claimed is:

1. A process for purifying 1,7'-dimethyl-2'-propyl-2,5'-bi-1H-benzimidazole which has been prepared by reacting 2-propyl-4-methyl-1H-benzimidazole-6-carboxylic acid with N-methyl-o-phenylene-diamine or a salt thereof in the presence of methanesulphonic acid and phosphorus pentoxide, said process comprising treating the crude product of said reaction with charcoal.

2. A process according to claim 1, wherein the reaction is carried out at a temperature of 125 to 145° C.

3. A process according to claim 1, wherein after the end of the reaction, the reaction mixture produced is subjected to hydrolysis and pH adjustment, and the reaction mixture is then added to the charcoal or charcoal is added to the reaction mixture.

4. A process according to claim 3, wherein the charcoal treatment is carried out at a temperature of 70 to 80° C.

5. A process according to claim 4, wherein the charcoal treatment is carried out at a pH of 0.7 to 1.2.

6. A process according to claim 3, wherein the quantity of charcoal used is from 5 to 20 percent by weight of the 2-propyl-4-methyl-1H-benzimidazole-6-carboxylic acid.

7. A process according to claim 3, wherein the charcoal treatment step is repeated one to three times after filtration or centrifugation of the reaction mixture.

8. A process according to claim 3, wherein after the treatment with charcoal, the following steps are carried out in succession:
   a) an organic solvent is added to the reaction mixture,
   b) a base is added to the reaction mixture to obtain a pH of 5 to 6,
   c) the aqueous phase is separated off, and
   d) the 1,7'-dimethyl-2'-propyl-2,5'-bi-1H-benzimidazole is isolated from the organic phase by crystallization and subsequent filtration or centrifugation.

9. A process according to claim 8, wherein isopropanol is used as the organic solvent in step a).

10. A process according to claim 8, wherein in step b), the base is added at a temperature of 70 to 80° C.

11. A process according to claim 8, wherein in step d), the crystallization is carried out by the addition of water.

* * * * *